(12) United States Patent
Berenguer Maimó et al.

(10) Patent No.: US 7,671,208 B2
(45) Date of Patent: Mar. 2, 2010

(54) ACETONE SOLVATE OF PHTHALOYL AMLODIPINE

(75) Inventors: Ramón Berenguer Maimó, Barcelona (ES); Jorge Medrano Rupérez, Barcelona (ES); Juan Francisco Merodio Cabanillas, Barcelona (ES)

(73) Assignee: Esteve Quimica, S.A., Barcelona (ES)

( * ) Notice: Subject to any disclaimer, the term of this patent is extended or adjusted under 35 U.S.C. 154(b) by 210 days.

(21) Appl. No.: 11/756,607

(22) Filed: May 31, 2007

(65) Prior Publication Data

US 2008/0242867 A1    Oct. 2, 2008

(30) Foreign Application Priority Data

Mar. 30, 2007  (EP) .................................. 07380086

(51) Int. Cl.
*C07D 401/12*     (2006.01)
(52) U.S. Cl. .................................. 546/277.1
(58) Field of Classification Search ............... 546/277.1
See application file for complete search history.

(56) References Cited

U.S. PATENT DOCUMENTS 4,572,908 A    2/1986  Campbell et al.

FOREIGN PATENT DOCUMENTS

| | | |
|---|---|---|
| DE | 202 01 878 U1 | 7/2002 |
| ES | 2 177 409 A1 | 12/2002 |
| HR | 20000490 | 2/2002 |
| HR | 20000490 A2 | 2/2002 |
| RU | 2 161 156 C1 | 12/2000 |
| WO | 00/47560 A2 | 8/2000 |
| WO | 01/02360 A1 | 1/2001 |
| WO | 02/053535 A2 | 7/2002 |
| WO | 2004/058711 A1 | 7/2004 |
| WO | 2005/023769 A1 | 3/2005 |
| WO | 20006/003672 A1 | 1/2006 |
| WO | 02/053135 A1 | 7/2007 |

OTHER PUBLICATIONS

English Language Summaries of Foreign Patent Documents RU2161156, ES2177409, HR20000490, and DE20201878.
Yathirajan, H.S., et al., "Phthaloyl amlodipine", "Acta Cryst.", Jan. 2005, pp. o175-o175, vol. E61, No. Pt. 1.

*Primary Examiner*—Patricia L Morris
(74) *Attorney, Agent, or Firm*—Steven J. Hultquist; Intellectual Property/Technology Law

(57) ABSTRACT

An acetone solvate of phthaloyl amlodipine, as well as a process for its preparation including dissolving phthaloyl amlodipine in acetone and cooling the mixture. The present invention also comprises a method for the synthesis of amlodipine, its salts or solvates, which comprises the use of an acetone solvate of phthaloyl amlodipine.

18 Claims, 2 Drawing Sheets

ACETONE SOLVATE OF PHTHALOYL AMLODIPINE

CROSS-REFERENCE TO RELATED APPLICATION

The priority of European Patent Application 073 80 086.4 filed Mar. 30, 2007 is hereby claimed under the provisions of 35 USC 119. The entire disclosure of said European Patent Application 073 80 086.4 is hereby incorporated herein in its entirety, for all purposes.

FIELD OF THE INVENTION

The present invention is directed to an acetone solvate of phthaloyl amlodipine, a process for its preparation and a method for the synthesis of amlodipine.

BACKGROUND OF THE INVENTION

Amlodipine besylate, also known as 2-{(2-aminoethoxy)-methyl-4-(2-chlorophenyl)-3-ethoxycarbonyl-5-methoxy-carbonyl-6-methyl-1,4-dihydropyridine}benzene sulfonate or 3-ethyl,5-methyl 2-((2-aminoethoxy)methyl)-4-(2-chlorophenyl)-1,4-dihydro-6-methylpyridine-3,5-dicarboxylate benzene sulfonate or 3-ethyl,5-methyl 2-[(2-aminoethoxy)methyl]-4-(2-chlorophenyl)-1,4-dihydro-6-methyl-3,5-pyridinedicarboxylate or 3-ethyl, 5-methyl 4-(2-chlorophenyl)-1,4-dihydro-6-methyl-2-(2-amino-ethoxymethyl)-3,5-pyridinedicarboxylate benzene sulfonate, is an anti-ischemic and anti-hypertensive drug.

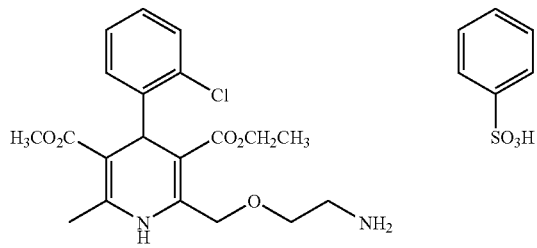

3-ethyl,5-methyl 2-[(2-aminoethoxy)methyl]-4-(2-chlorophenyl)-1,4-dihydro-6-methyl-3,5-pyridinedicarboxylate; or Amlodipine besylate A number of syntheses have been described for the synthesis of amlodipine besylate in which the key intermediate is phthaloyl amlodipine, also known as 4-(2-chlorophenyl)-3-ethoxycarbonyl-5-methoxycarbonyl-6-methyl-2-(2-phtalimidoethoxy)-methyl-1,4-dihydropyridine or 3-ethyl, 5-methyl 4-(2-chlorophenyl)-1,4-dihydro-6-methyl-2-[(2-phthalimidoethoxy)methyl]-3,5-pyridinedicarboxylate.

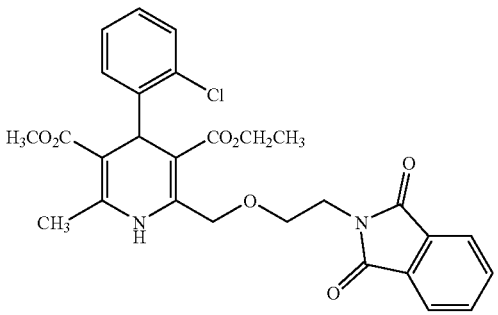

3-ethyl, 5-methyl 4-(2-chlorophenyl)-1,4-dihydro-6-methyl-2-[(2-phthalimidoethoxy)methyl]-3,5-pyridinedicarboxylate; or Phthaloyl amlodipine Thus, providing phthaloyl amlodipine in good yield and high purity is a central issue in the synthesis of amlodipine, especially for the synthesis of amlodipine besylate.

In U.S. Pat. No. 4,572,909 phthaloyl amlodipine is obtained by condensation of phthalic anhydride with the corresponding free amine or condensation of 2-chlorobenzaldehyde, 4-[2-(phthalimido)ethoxy]acetoacetate and methyl 3-aminocrotonate. Purification of phthaloyl amlodipine is carried out by precipitation from acetic acid, followed by resuspension in methanol.

In WO00/24714 phthaloyl amlodipine is obtained by condensation between ethyl 3-amino-4-(2-phthalimidoetoxy) crotonate and methyl 2-(2-chlorobenzyliden)acetoacetate. Purification is carried out by recrystallization in methanol, ethanol, isopropanol, toluene or xylene.

In JP20001002677 phthaloyl amlodipine is purified by recrystallization in an organic solvent in the presence of acetic acid. In WO02053135 phthaloyl amlodipine is purified by a first recrystallizing in acetic acid, resuspending in methanol and finally by recrystallization from ethyl acetate.

U.S. Pat. No. 6,784,297 describes a process for the synthesis of amlodipine besylate starting from phthalic anhydride and comprising phthaloyl amlodipine as intermediate (step d)). Phthaloyl amlodipine is subsequently purified in step e) in a two step sequence which comprises (i) dissolving it in an organic solvent in the ratio 1:2-1:5 w/v followed by (ii) precipitation by the addition of water at 35-60° C. According to a preferred embodiment, the solvent in step (i) is acetone. The free phthaloyl amlodipine obtained is then transformed into its base and then into amlodipine besylate.

The purification methods of the prior art required complicated purification methods and are not capable of removing all the impurities to the levels required by applicable regulations.

SUMMARY OF THE INVENTION

Figure 1:
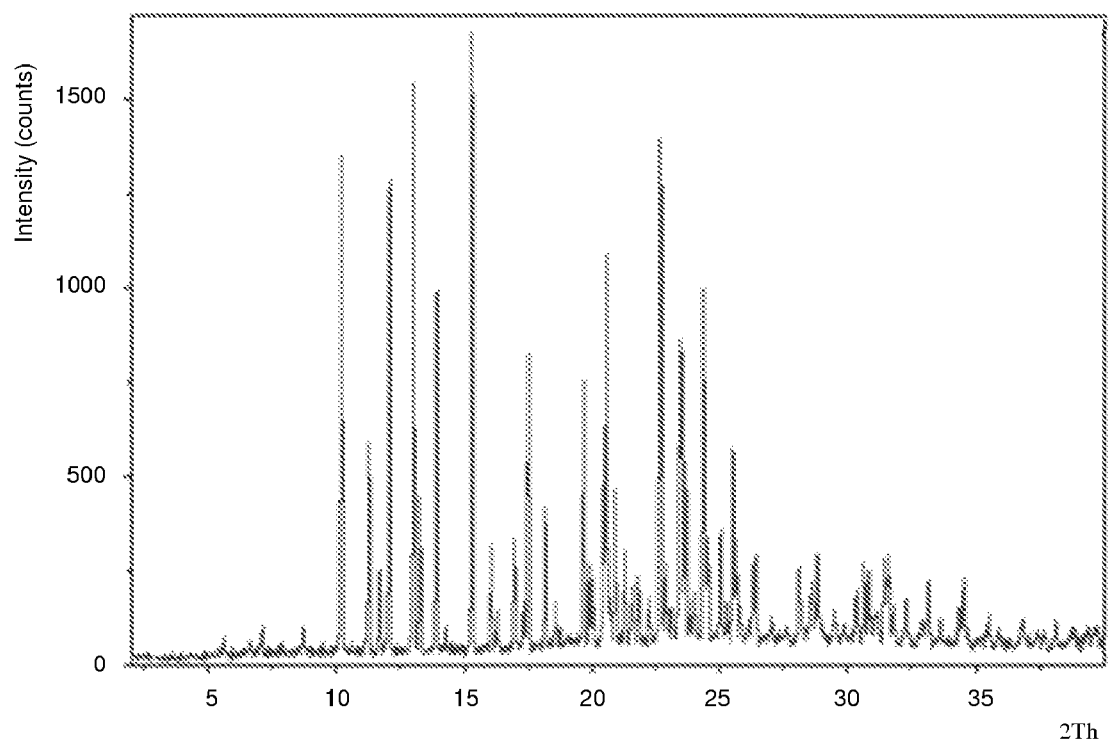
FIG. 1 shows an X-ray powder diffractogram of the acetone solvate of the invention. The abscissa axis shows the 2θ angles and the ordinate axis shows the intensity.

The inventors have now surprisingly found that the provision of an acetone solvate of phthaloyl amlodipine provides an excellent method for the purification of phthaloyl amlodipine.

Recrystallization of phthaloyl amlodipine from acetone and further cooling provides an acetone solvate of phthaloyl amlodipine with high purity and yield, and without the need of using complicated work-up methods. Additionally, the acetone solvate of phthaloyl amlodipine shows a high degree of crystallinity, which makes it easy to manipulate and store. The acetone solvate of phthaloyl amlodipine of the invention has excellent solubility and may be used to obtain amlodipine with high purity.

Thus, according to a first aspect, the present invention is directed to an acetone solvate of 3-ethyl, 5-methyl 4-(2-chlorophenyl)-1,4-dihydro-6-methyl-2-[(2-phthalimidoethoxy)methyl]-3,5-pyridinedicarboxylate.

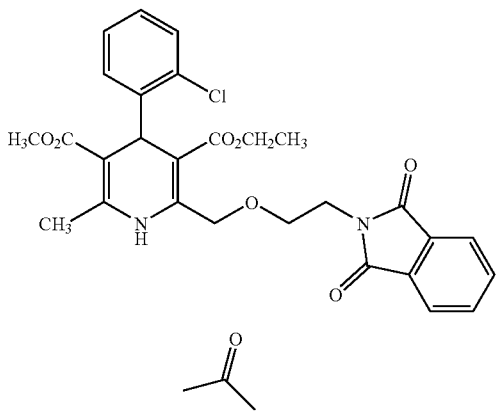

Acetone solvate of 3-ethyl, 5-methyl 4-(2-chlorophenyl)-1,4-dihydro-6-methyl-2-[(2-phthalimidoethoxy) methyl]-3,5-pyridinedicarboxylate; or Acetone solvate of Phthaloyl amlodipine According to a second aspect, the present invention is directed to a process for the synthesis of the acetone solvate of 3-ethyl, 5-methyl 4-(2-chlorophenyl)-1,4-dihydro-6-methyl-2-[(2-phthalimidoethoxy)methyl]-3,5-pyridinedicarboxylate, which comprises
  a) dissolving 3-ethyl, 5-methyl 4-(2-chlorophenyl)-1,4-dihydro-6-methyl-2-[(2-phthalimidoethoxy)methyl]-3,5-pyridinedicarboxylate in acetone at a temperature comprised between above 20° C. and reflux; and
  b) cooling the mixture to a temperature comprised between −10° C. and 20° C. in order to precipitate the acetone solvate of 3-ethyl, 5-methyl 4-(2-chlorophenyl)-1,4-dihydro-6-methyl-2-[(2-phthalimidoethoxy)methyl]-3,5-pyridinedicarboxylate.

According to a third aspect, the present invention is directed to a method for the synthesis of 3-ethyl, 5-methyl 2-((2-aminoethoxy)methyl)-4-(2-chlorophenyl)-1,4-dihydro-6-methylpyridine-3,5-dicarboxylate, its salts or solvates thereof, preferably its benzene sulfonate salt (amlodipine besylate), which comprises the use of an acetone solvent of 3-ethyl, 5-methyl 4-(2-chlorophenyl)-1,4-dihydro-6-methyl-2-[(2-phthalimidoethoxy)methyl]-3,5-pyridinedicarboxylate, as defined herein, as a starting material or as an intermediate.

DETAILED DESCRIPTION OF THE INVENTION

Synthesis of the Acetone Solvate of Phthaloyl Amlodipine

Contrary to the method described in U.S. Pat. No. 6,784,297, the method of the invention does not comprise the addition of water. Instead, once the phthaloyl amlodipine is dissolved in acetone, the mixture is allowed to cool to a temperature comprised between −10° C. and 20° C. The inventors have found that in this range of temperatures, the desired acetone solvate of phthaloyl amlodipine is readily obtained in good yields and high purity. According to a preferred embodiment, the mixture is cooled in step b) at a temperature comprised between −5° C. and 5° C.

It has been observed that excellent results are obtained when cooling in step b) is performed in two steps. According to a preferred embodiment, cooling in step b) is performed in two steps: a first cooling to a temperature comprised between above 5° C. and 20° C. and a second cooling to a temperature comprised between −10° C. and 5° C.

According to one preferred embodiment, said first cooling comprises a temperature between 7° C. and 15° C.

According to another preferred embodiment, said first cooling comprises a temperature between 10° C. and 15° C.

According to yet another preferred embodiment, said first cooling comprises a temperature between 8° C. and 12° C.

According to one preferred embodiment, said second cooling comprises a temperature between 0° C. and 5° C.

The temperature to which phthaloyl amlodipine is heated or the concentration of phthaloyl amlodipine in step a) of the process is not critical. The only requirement is that phthaloyl amlodipine is dissolved. Therefore, the higher the temperature and/or the lower the concentration, the more readily phthaloyl amlodipine is dissolved.

According to one preferred embodiment, the temperature in step a) is comprised between 30° C. and reflux. According to another preferred embodiment, the temperature in step a) is comprised between 40° C. and reflux.

According to one preferred embodiment, the concentration of phthaloyl amolodipine in step a) is comprised between 0.02 and 0.3 g/ml, preferably between 0.04 and 0.2 g/ml.

The above mentioned process requires no seeding with preformed crystals of the acetone solvate of phthaloyl amlodipine. However, the process of the invention may also include such possibility. Thus, according to a preferred embodiment, the process of the invention comprises the additional step, between step a) and step b), of seeding the mixture with a crystal of an acetone solvate of 3-ethyl, 5-methyl 4-(2-chlorophenyl)-1,4-dihydro-6-methyl-2-[(2-phthalimidoethoxy)methyl]-3,5-pyridinedicarboxylate. Such preferred embodiment comprises the following steps:
  a) dissolving 3-ethyl, 5-methyl 4-(2-chlorophenyl)-1,4-dihydro-6-methyl-2-[(2-phthalimidoethoxy)methyl]-3,5-pyridinedicarboxylate in acetone at a temperature comprised between above 20° C. and reflux;
  b) seeding the mixture with a crystal of an acetone solvate of 3-ethyl, 5-methyl 4-(2-chlorophenyl)-1,4-dihydro-6-methyl-2-[(2-phthalimidoethoxy) methyl]-3,5-pyridinedicarboxylate in order to precipitate the acetone solvate; and c) cooling the mixture to a temperature comprised between −10° C. and 20° C. in order to isolate the acetone solvate of 3-ethyl, 5-methyl 4-(2-chlorophenyl)-1,4-dihydro-6-methyl-2-[(2-phthalimidoethoxy)methyl]-3,5-pyridinedicarboxylate.

According to another preferred embodiment, the process comprises
a) dissolving 3-ethyl, 5-methyl 4-(2-chlorophenyl)-1,4-dihydro-6-methyl-2-[(2-phthalimidoethoxy)methyl]-3,5-pyridinedicarboxylate in acetone at a temperature comprised between 50° C. and reflux;
b) cooling the mixture to a temperature comprised between 30° C. and 45° C.;
c) seeding the mixture with a crystal of the acetone solvate of 3-ethyl, 5-methyl 4-(2-chlorophenyl)-1,4-dihydro-6-methyl-2-[(2-phthalimidoethoxy)methyl]-3,5-pyridinedicarboxylate in order to precipitate the acetone solvate; and
d) cooling the mixture to a temperature comprised between −10° C. and 20° C. in order to isolate the acetone solvate of 3-ethyl, 5-methyl 4-(2-chlorophenyl)-1,4-dihydro-6-methyl-2-[(2-phthalimidoethoxy)methyl]-3,5-pyridinedicarboxylate.

The process of the invention provides phthaloyl amlodipine with high purity, even with regard to impurities which are difficult to remove with other purification methods. For example, in the process described in example 1 below, phthaloyl amlodipine is obtained in 70% yield and a purity of 98.6%. Such process comprises the steps of a) condensation between (Z)-methyl 2-(2-chlorobenzylidene)-3-oxobutanoate and ethyl 3-amino-4-[2-(phthalimido)ethoxy]crotonate, and b) isolation of phthaloyl amlodipine. One of the main impurities obtained is impurity HA

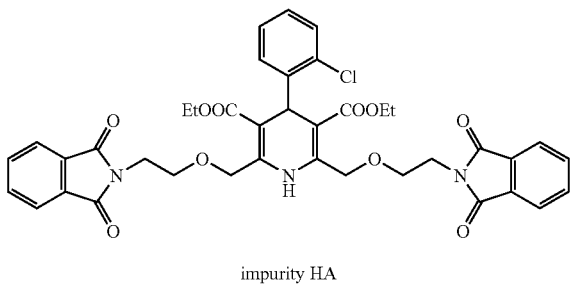

impurity HA that is, 4-(2-Chloro-phenyl)-2,6-bis-[2-(1,3-dioxo-1,3-dihydro-isoindol-2-yl)-ethoxymethyl]-1,4-dihydro-pyridine-3,5-dicarboxylic acid diethyl ester or ethyl 2,6-bis[2-(phthalimidoethoxy)methyl]-4-(2-chlorophenyl)-1,4-dihydro-3,5-pyridine dicarboxylate (named "impurity HA" for the purposes of the present invention). As shown in examples 4 to 10, the provision of the acetone solvate of phthaloyl amlodipine significantly reduces the levels of impurity HA.

The concentration of other impurities is also significantly reduced when forming the acetone solvate of phthaloyl amlodipine.

Characterization of the Acetone Solvate of Phthaloyl Amlodipine

The acetone solvate of phthaloyl amlodipine obtainable by the process of the invention was characterized by X-ray powder diffractogram, thermogravimetric analysis (TG), differential scanning calorimetry (DSC) and infrared spectrum (IR).

X-Ray diffractograms were obtained using a PANalytycak X'Pert PRO MPD diffractometer with a goniometer θ/θ, radiation CuKα, λ=1.5406 Å

The DSC measurements were carried out at a scan rate of 2° C./minute from 40° C. to 170° C. with a Mettler Toledo DSC822$^e$ Thermogravimetric analysis measurements were carried out at a scan rate of 5° C./minute from 25° C. to 200° C. with a Mettler Toledo TGA/STDA 851$^e$.

Fourier transform infrared spectra were acquired on a Perkin Elmer Spectrum One. Sample preparations were performed as KBr disk.

X-Ray Powder Diffractogram

The acetone solvate of phthaloyl amlodipine shows an X-ray powder diffractogram having relevant peaks expressed as 2θ angles at about 10.2, 12.1, 13.0, 13.9, 15.3, 17.5, 19.7, 20.6, 22.7, 23.5 and 24.4°. A complete X-ray powder diffractogram is shown in FIG. 1 and a complete peak pattern is shown in Table 1 (peaks with an intensity below 5% are not shown).

TABLE 1

| Pos. (° 2Th.) | d (Å) | Rel Int. (%) |
|---|---|---|
| 10.2 | 8.6 | 82 |
| 11.3 | 7.8 | 36 |
| 11.7 | 7.6 | 14 |
| 12.1 | 7.3 | 82 |
| 13.0 | 6.8 | 95 |
| 13.3 | 6.7 | 25 |
| 13.9 | 6.3 | 61 |
| 15.3 | 5.8 | 100 |
| 16.1 | 5.5 | 18 |
| 16.3 | 5.4 | 6 |
| 17.0 | 5.2 | 19 |
| 17.3 | 5.1 | 7 |
| 17.5 | 5.1 | 48 |
| 18.2 | 4.9 | 23 |
| 18.6 | 4.8 | 7 |
| 19.7 | 4.5 | 46 |
| 19.9 | 4.5 | 13 |
| 20.0 | 4.4 | 10 |
| 20.4 | 4.3 | 27 |
| 20.6 | 4.3 | 67 |
| 20.8 | 4.3 | 7 |
| 20.9 | 4.2 | 27 |
| 21.3 | 4.2 | 16 |
| 21.6 | 4.1 | 10 |
| 21.8 | 4.1 | 12 |
| 22.3 | 4.0 | 7 |
| 22.7 | 3.9 | 88 |
| 22.9 | 3.9 | 12 |
| 23.4 | 3.8 | 31 |
| 23.5 | 3.8 | 52 |
| 23.6 | 3.8 | 30 |
| 23.9 | 3.7 | 6 |
| 24.0 | 3.7 | 7 |
| 24.4 | 3.7 | 59 |
| 24.5 | 3.6 | 17 |
| 25.0 | 3.6 | 18 |
| 25.3 | 3.5 | 6 |
| 25.5 | 3.5 | 32 |
| 25.7 | 3.5 | 17 |
| 25.8 | 3.5 | 5 |
| 26.3 | 3.4 | 12 |
| 26.4 | 3.4 | 13 |
| 28.1 | 3.2 | 11 |
| 28.6 | 3.1 | 10 |
| 28.8 | 3.1 | 14 |
| 30.4 | 2.9 | 8 |
| 30.6 | 2.9 | 13 |
| 30.8 | 2.9 | 11 |
| 31.4 | 2.8 | 14 |
| 31.6 | 2.8 | 15 |

TABLE 1-continued

| Pos. (° 2Th.) | d (Å) | Rel Int. (%) |
|---|---|---|
| 32.2 | 2.8 | 7 |
| 33.1 | 2.7 | 11 |
| 34.3 | 2.6 | 6 |
| 34.5 | 2.6 | 11 |
| 35.5 | 2.5 | 5 |

Differential Scanning Calorimetry (DSC)

The acetone solvate of phthaloyl amlodipine obtainable by the process of the invention shows an endothermal peak around 80° C., between 75° C. and 85° C.

Thermogravimetric Analysis

The acetone solvate of phthaloyl amlodipine obtainable by the process of the invention shows a total weight loss of about 10.4%, between 7 and 12% w/w. The theoretical acetone content of a sample is 9.7%.

Infrared Spectrum (IR)

Figure 2:
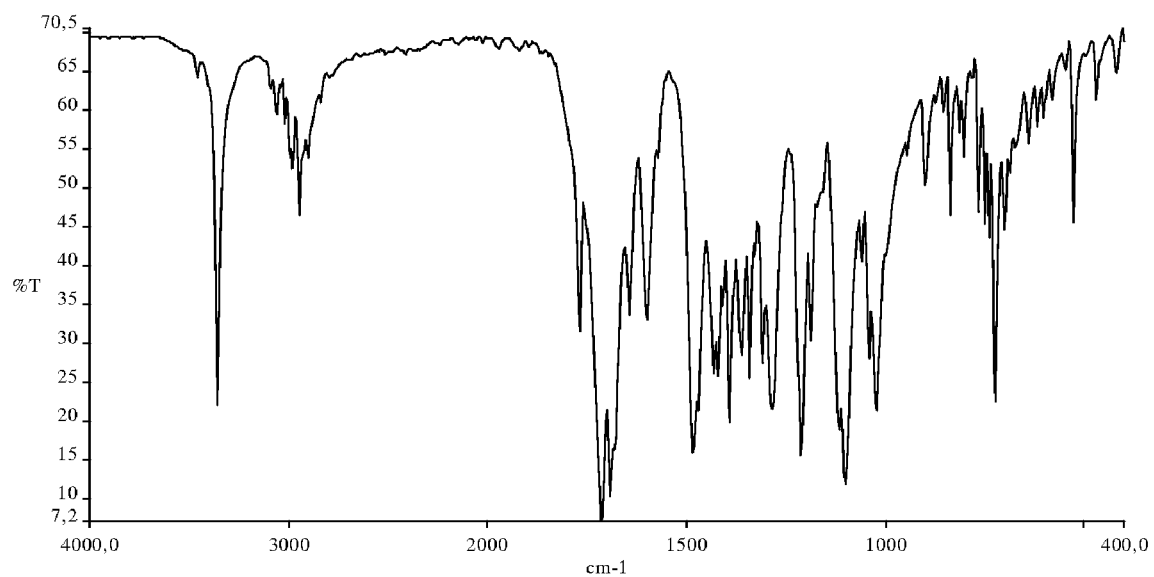
FIG. 2 shows an Infrared Spectrum of the acetone solvate of the invention. The abscissa axis shows the frequency (cm$^{-1}$) and the ordinate axis shows the transmittance (% T).

The acetone solvate of phthaloyl amlodipine showed an IR spectrum having relevant peaks expressed in cm$^{-1}$ at about 3361, 2949, 1769, 1714, 1693, 1644, 1601, 1484, 1433, 1421, 1394, 1363, 1343, 1311, 1287, 1213, 1118, 1102, 1042, 1025, 727, 530 cm$^{-1}$. A complete IR is shown in FIG. 2.

Method for the Synthesis of Amlodipine Besylate

As mentioned above, the acetone solvate of phthaloyl amlodipine is obtained in high yields and excellent purity. The acetone solvate can then be readily liberated in order to obtain free phthaloyl amlodipine or it can be used directly.

Therefore, an aspect of the present invention is a method for the synthesis of 3-ethyl, 5-methyl 2-((2-aminoethoxy)methyl)-4-(2-chlorophenyl)-1,4-dihydro-6-methylpyridine-3,5-dicarboxylate (amlodipine), its salts or solvates thereof which comprises the use of an acetone solvent of 3-ethyl, 5-methyl 4-(2-chlorophenyl)-1,4-dihydro-6-methyl-2-[(2-phthalimidoethoxy)methyl]-3,5-pyridinedicarboxylate (acetone solvate of phthaloyl amlodipine) as defined above as a starting material or as intermediate

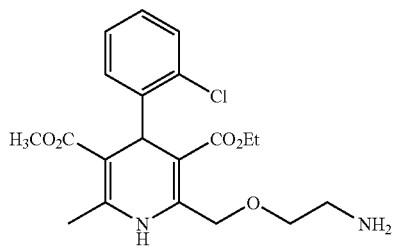

3-ethyl,5-methyl 2-((2-aminoethoxy)methyl)-4-(2-chlorophenyl)-1,4-dihydro-6-methylpyridine-3,5-dicarboxylate Preferably, such method is for the synthesis of 3-ethyl, 5-methyl 2-[(2-aminoethoxy)methyl]-4-(2-chlorophenyl)-1,4-dihydro-6-methyl-3,5-pyridinedicarboxylate.

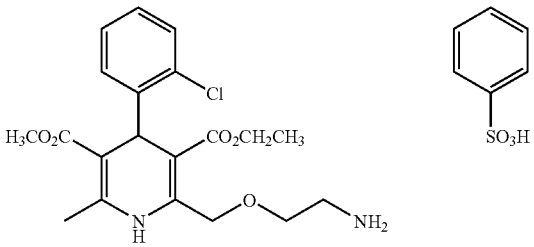

3-ethyl, 5-methyl 2-[(2-aminoethoxy)methyl]-4-(2-chlorophenyl)-1,4-dihydro-6-methyl-3,5-pyridinedicarboxylate For example, the acetone solvate of phthaloyl amlodipine may be used as the starting material in the synthesis of amlodipine following any of the methods described in the prior art. For example, amlodipine besylate may be obtained using the acetone solvate of phthaloyl amlodipine by the method described in U.S. Pat. No. 6,784,297.

EXAMPLES

Example 1

Preparation of Phthaloyl Amlodipine

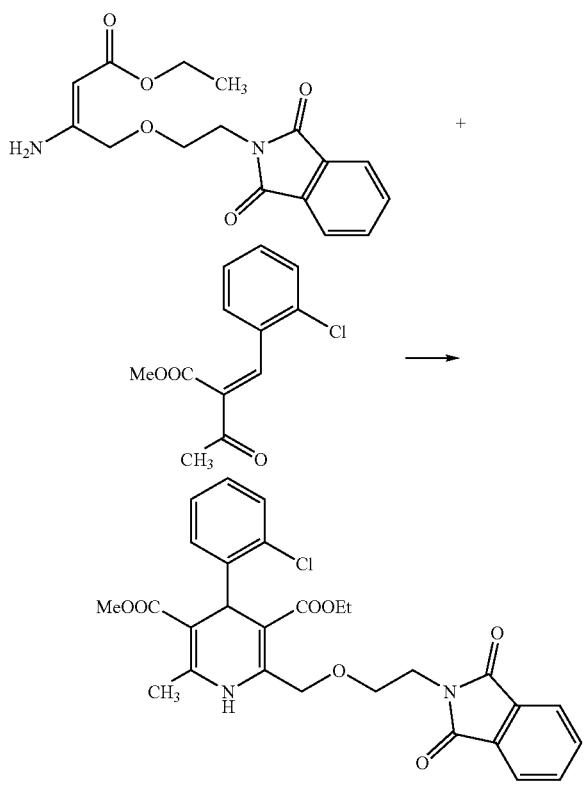

Methyl 2-(2-chlorobenzyliden)acetoacetate (40.6 g; 169.9 mmol) was condensed with ethyl 3-amino-4-[2-(phthalimido)ethoxy]crotonate (51.5 g; 161.8 mmol) in 2-propanol (160 ml) under reflux for 11 hours. Methanol (103 ml) was added and mixture was cooled to 5/0° C. The solid was filtered off and dried at 40° C. Phthaloyl Amlodipine (60.7 g, purity: 98.6%; 0.86% of impurity HA) was obtained.

Preparation of the Acetone Solvate of Phthaloyl Amlodipine

Examples 2 and 3 illustrate the method of synthesis of the acetone solvate of phthaloyl amlodipine.

Example 2

Preparation of Solvate without Seeding

Phthaloyl amlodipine (10 g, purity: 95.4%) was dissolved in 50 ml of acetone under reflux. Once solution was complete, it was cooled slowly to 15/10° C. Then the solution was cooled to 5/0° C. and the solid was filtered off and washed with cold acetone. The product was dried under vacuum. Yield of Phthaloyl amlodipine acetone solvate: 9.2 g. Purity: 98.9%.

$^1$H-NMR (400 MHz, DMSO-$d_6$) $\delta$(ppm): 8.29 (broad singlet, 1H); 7.85 (m, 4H); 7.27 (dd, J: 7.7 Hz, J': 1.8 Hz, 1H); 7.24 (dd, J: 7.7 Hz, J': 1.3 Hz, 1H); 7.20 (dt, J: 7.2 Hz, J': 1.3 Hz, 1H); 7.10 (dt, J: 7.2 Hz, J': 1.8 Hz, 1H); 5.23 (s, 1H); 4.63 (d, J: 14.2 Hz, 1H); 4.50 (d, J: 14.2 Hz, 1H); 3.92 (m, 2H); 3.82 (m, 2H); 3.70 (m, 2H); 3.47 (s, 3H); 2.19 (s, 3H); 2.08 (s, 6H); 1.07 (t, J: 7.1 Hz, 3H).

IR 3361, 2949, 1769, 1714, 1693, 1644, 1601, 1484, 1433, 1421, 1394, 1363, 1343, 1311, 1287, 1213, 1118, 1102, 1042, 1025, 727, 530 cm$^{-1}$.

Example 3

Solvate with Seed

Phthaloyl amlodipine (10 g, purity: 98.6%) was dissolved in 60 ml of acetone under reflux. Then the solution is cooled to 45/30° C. and seeded with Phthaloyl amlodipine acetone solvate to allow precipitation. The suspension was then cooled to 5/0° C., filtered off and washed with cold acetone. The solid was dried under vacuum. Yield of Phthaloyl amlodipine acetone solvate: 10.5 g. Purity: 99.9%.

Examples 4 to 10

The following examples 4 to 6 further illustrate the method of synthesis of the acetone solvate of phthaloyl amlodipine. The comparative examples (examples 7 to 10) correspond to examples 1 to 4 of U.S. Pat. No. 6,784,297, respectively, and have been prepared for comparative purposes. As shown in examples 7 to 10 below, the process according to U.S. Pat. No. 6,784,297 does not provide the acetone solvate of phthaloyl amlodipine.

In order to compare the purity of the compounds obtained by the method of the invention, the levels of impurity HA have been measured in examples 4 to 10. As shown below, the provision of the acetone solvate of phthaloyl amlodipine according to the present invention yields a final product with higher levels of purity compared to the method disclosed in U.S. Pat. No. 6,784,297. A similar trend has been observed with other impurities.

Example 4

Preparation of Solvate without Seed

Phthaloyl amlodipine (10 g, purity: 95.4%; 1.06% of impurity HA) was dissolved in 50 ml of acetone under reflux. Once solution was complete, it was cooled slowly to 15/10° C. Then the solution was cooled to 5/0° C. and the solid was filtered off and washed with cold acetone.

The product was dried under vacuum at room temperature.
Yield of Phthaloyl amlodipine acetone solvate: 9.2 g.
DSC peak: 79.3° C.
Purity: 98.9%; 0.08% of impurity HA.

Example 5

Preparation of Solvate without Seed

Phthaloyl amlodipine (10 g, purity: 92.8%; 1.90% of impurity HA) was dissolved in 173 ml of acetone at 32° C. Once solution was complete, it was cooled to 12/8° C. until precipitation. Then the slurry was cooled to 5/0° C. and the solid was filtered off and washed with cold acetone.

The product was dried under vacuum at room temperature.
Yield of Phthaloyl amlodipine acetone solvate: 8.2 g.
DSC peak: 79.1° C.
Purity: 99.5%; 0.14% of impurity HA.

Example 6

Preparation of Solvate with Seed

Phthaloyl amlodipine (10 g, purity: 98.6%; 0.86% of impurity HA) was dissolved in 60 ml of acetone under reflux. Then the solution is cooled to 45/30° C. and seeded with Phthaloyl amlodipine acetone solvate to allow precipitation. The suspension was then cooled to 5/0° C. and water (5 ml) was added. The solid was filtered off, washed with acetone and dried under vacuum at room temperature.

Yield of Phthaloyl amlodipine acetone solvate: 10.4 g (8.1% w/w of acetone).
DSC peak: 81.3° C.
Purity: 99.94%; 0.01% of impurity HA.

COMPARATIVE EXAMPLES

Example 7

Example 1 of U.S. Pat. No. 6,784,297

Phthaloyl amlodipine (10 g, purity: 98.6%; 0.86% of impurity HA) was dissolved in 35 ml of acetone at reflux and cooled to 45° C. Water (10 ml) was slowly added to precipitate the product which was cooled to 5/0° C. and dried under vacuum at room temperature.

Yield: 9.3 g (<0.3% w/w of acetone).
DSC peak: 135.8° C.
Purity: 99.0%. 0.83% of impurity HA

Example 8

Example 2 of U.S. Pat. No. 6,784,297

Phthaloyl amlodipine (10 g, purity: 98.6%; 0.86% of impurity HA) was dissolved in 50 ml of acetone at 45° C. and 14 ml of water was slowly added to precipitate the product which was cooled to 5/0° C. and dried under vacuum.

Yield: 9.5 g (<0.3% w/w of acetone).
DSC peak: 135.5° C.
Purity: 98.9%. 0.84% of impurity HA

Example 9

Example 3 of U.S. Pat. No. 6,784,297

Phthaloyl amlodipine (10 g, purity: 98.6%; 0.86% of impurity HA) was slurried in 25 ml of acetone, heated to reflux for 15 min and cooled to 45° C. Water (9 ml) was slowly added to precipitate the product which was cooled to 5/0° C. and dried under vacuum at room temperature.

Yield: 9.5 g (<0.3% w/w of acetone).
DSC peak: 136.3° C.
Purity: 99.2%. 0.60% of impurity HA

Example 10

Example 4 of U.S. Pat. No. 6,784,297

Phthaloyl amlodipine (10 g, purity: 98.6%; 0.86% of impurity HA) was dissolved in 50 ml of acetone at 45° C. and 15 ml of water was slowly added to precipitate the product which was cooled to 5/0° C. and dried under vacuum at room temperature.

Yield: 8.7 g (<0.3% w/w of acetone).
DSC peak: 135.5° C.
Purity: 99.0%. 0.83% of impurity HA Results obtained in Examples 4 to 10 are summarized in Table 2

TABLE 2

| Example | Starting Phthaloyl Amlodipine | | Experimental | | | | Analytical data | | |
|---|---|---|---|---|---|---|---|---|---|
| | Purity % | Impurity HA, % | Ratio acetone/ Phthaloyl Amlodipine | Reaction Temp | 1st Cooling Temp | 2nd Cooling Temp | DSC Peak (° C.) | Purity % | Impurity HA, % |
| 4 | 95.4 | 1.06 | 1:5 | Reflux | 10-15° C. No seed | 5-0° C. | 79.3 | 98.9 | 0.08 |
| 5 | 92.8 | 1.90 | 1:17 | 32° C. | 8-12° C. No seed | 5-0° C. | 79.1 | 99.5 | 0.14 |
| 6 | 98.6 | 0.86 | 1:6 | Reflux | 30-45° C. seeding | 5-0° C. | 81.3 | 99.9 | 0.01 |
| 7 | 98.6 | 0.86 | 1:3.5 | Reflux | 45° C. + $H_2O$ | 5-0° C. | 135.8 | 99.0 | 0.83 |
| 8 | 98.6 | 0.86 | 1:5 | 45° C. + $H_2O$ | — | 5-0° C. | 135.5 | 98.9 | 0.84 |
| 9 | 98.6 | 0.86 | 1:2.5 | Reflux | 45° C. + $H_2O$ | 5-0° C. | 136.3 | 99.2 | 0.60 |
| 10 | 98.6 | 0.86 | 1:5 | 45° C. + $H_2O$ | — | 5-0° C. | 135.5 | 99.0 | 0.83 |

(iv) an IR spectrum having relevant peaks expressed in $cm^{-1}$ at about 3361, 2949, 1769, 1714, 1693, 1644, 1601, 1484, 1433, 1421, 1394, 1363, 1343, 1311, 1287, 1213, 1118, 1102, 1042, 1025, 727, 530.

3. An acetone solvate of 3-ethyl, 5-methyl 4-(2-chlorophenyl)-1,4-dihydro-6-methyl-2-[(2-phthalimidoethoxy)methyl]-3,5-pyridinedicarboxylate according to claim 2, which shows an X-ray powder diffractogram substantially similar to that shown in FIG. 1.

4. An acetone solvate of 3-ethyl, 5-methyl 4-(2-chlorophenyl)-1,4-dihydro-6-methyl-2-[(2-phthalimidoethoxy)methyl]-3,5-pyridinedicarboxylate according to claim 2, which shows an IR spectrum substantially similar to that shown in FIG. 2.

5. A process for the synthesis of an acetone solvate of 3-ethyl, 5-methyl 4-(2-chlorophenyl)-1,4-dihydro-6-methyl-2-[(2-phthalimidoethoxy)methyl]-3,5-pyridinedicarboxylate as defined in claim 1, which comprises:

a) dissolving 3-ethyl, 5-methyl 4-(2-chlorophenyl)-1,4-dihydro-6-methyl-2-[(2-phthalimidoethoxy)methyl]-3,5-pyridinedicarboxylate in acetone at a temperature comprised between above 20° C. and reflux; and b) cooling the mixture to a temperature comprised between −10° C. and 20° C.

6. A process according to claim 5, wherein the temperature in step a) is comprised between 30° C. and reflux.

The invention claimed is:

1. An acetone solvate of 3-ethyl, 5-methyl 4-(2-chlorophenyl)-1,4-dihydro-6-methyl-2-[(2-phthalimidoethoxy)methyl]-3,5-pyridinedicarboxylate.

2. An acetone solvate of 3-ethyl, 5-methyl 4-(2-chlorophenyl)-1,4-dihydro-6-methyl-2-[(2-phthalimidoethoxy)methyl]-3,5-pyridinedicarboxylate according to claim 1, characterized by at least one of:

(i) an X-ray powder diffractogram pattern having peaks expressed as 2θ angles at about 10.2, 12.1, 13.0, 13.9, 15.3, 17.5, 19.7, 20.6, 22.7, 23.5 and 24.4°;

(ii) a weight loss after a thermogravimetric analysis comprised between 7 and 12% w/w;

(iii) an endotherm peak in a differential scanning calorimetry diagram at a temperature comprised between 75° C. and 85° C.; and 7. A process according to claim 6, wherein the temperature in step a) is comprised between 40° C. and reflux.

8. A process according to claim 5, wherein the concentration of phthaloyl amlodipine in step a) is comprised between 0.02 and 0.3 g/ml.

9. A process according to claim 5, wherein cooling in step b) is performed in two steps: a first cooling to a temperature comprised between above 5° C. and 20° C. and a second cooling to a temperature comprised between −10° C. and 5° C.

10. A process according to claim 9, wherein said first cooling comprises a temperature between 7° C. and 15° C.

11. A process according to claim 10, wherein said first cooling comprises a temperature between 10° C. and 15° C.

12. A process according to claim 10, wherein said first cooling comprises a temperature between 8° C. and 12° C.

13. A process according to claim 9, wherein said second cooling comprises a temperature between 0° C. and 5° C.

14. A process according to claim 5, which comprises the additional step between step a) and step b) of seeding the mixture with a crystal of an acetone solvate of 3-ethyl, 5-methyl 4-(2-chlorophenyl)-1,4-dihydro-6-methyl-2-[(2-phthalimidoethoxy)methyl]-3,5-pyridinedicarboxylate.

15. A process according claim 14, wherein
   a) the 3-ethyl, 5-methyl 4-(2-chlorophenyl)-1,4-dihydro-6-methyl-2-[(2-phthalimidoethoxy)methyl]-3,5-pyridinedicarboxylate is dissolved in acetone at a temperature comprised between 50° C. and reflux, to form a mixture;
   b) the mixture is cooled to a temperature comprised between 30° C. and 45° C.;
   c) the mixture is seeded with a crystal of the acetone solvate of 3-ethyl, 5-methyl 4-(2-chlorophenyl)-1,4-dihydro-6-methyl-2-[(2-phthalimidoethoxy)methyl]-3,5-pyridinedicarboxylate; and
   d) the mixture is cooled to a temperature comprised between −10° C. and 20° C.

16. A process according to claim 5, wherein the mixture is cooled in step b) at a temperature comprised between −5° C. and 5° C.

17. A method of use of an acetone solvate of 3-ethyl, 5-methyl 4-(2-chlorophenyl)-1,4-dihydro-6-methyl-2-[(2-phthalimidoethoxy)methyl]-3,5-pyridinedicarboxylate, comprising reaction of said acetone solvate in a synthesis reaction for the production of 3-ethyl,5-methyl 2-((2-aminoethoxy)methyl)-4-(2-chlorophenyl)-1,4-dihydro-6-methyl-3,5-pyridinedicarboxylate, its salts or solvates thereof.

18. A method according to claim 17, for the synthesis of 3-ethyl,5-methyl 2-[(2-aminoethoxy)methyl]-4-(2-chlorophenyl)-1,4-dihydro-6-methyl-3,5-pyridinedicarboxylate, of the formula:

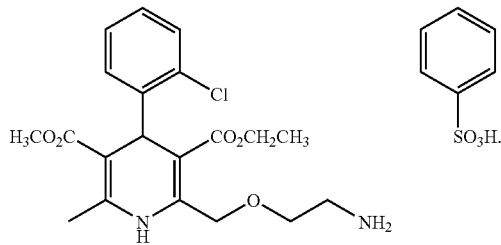

* * * * *

UNITED STATES PATENT AND TRADEMARK OFFICE
CERTIFICATE OF CORRECTION

| | | |
|---|---|---|
| PATENT NO. | : 7,671,208 B2 | Page 1 of 1 |
| APPLICATION NO. | : 11/756607 | |
| DATED | : March 2, 2010 | |
| INVENTOR(S) | : Ramon Berenguer Maimó | |

It is certified that error appears in the above-identified patent and that said Letters Patent is hereby corrected as shown below:

Page 1, first column, Foreign Application Priority Data, "07380086" should be -- 07380086.4 --.

Page 1, References Cited, Foreign Patent Documents, second column, add: -- WO 02/053135 A1 7/2002 --.

Page 1, References Cited, Foreign Patent Documents, second column, "WO 20006/003672" should be -- WO 2006/003672 --.

Signed and Sealed this

Thirteenth Day of July, 2010

David J. Kappos
*Director of the United States Patent and Trademark Office*